United States Patent [19]

Hall

[11] Patent Number: 4,607,049

[45] Date of Patent: Aug. 19, 1986

[54] 7-OXABICYCLOHEPTANE SUBSTITUTED THIO PROSTAGLANDIN ANALOGS USEFUL IN THE TREATMENT OF THROMBOLYTIC DISEASE

[75] Inventor: Steven E. Hall, Ewing Township, Mercer County, N.J.

[73] Assignee: E. R. Squibb & Sons, Inc., Princeton, N.J.

[21] Appl. No.: 725,978

[22] Filed: Apr. 22, 1985

[51] Int. Cl.$^4$ .................. A61K 31/557; A61K 31/34; C07D 307/00

[52] U.S. Cl. ..................... 514/469; 549/463

[58] Field of Search .................. 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,456,616 | 6/1984 | Haslanger | 549/463 |
| 4,474,803 | 10/1984 | Hall | 549/463 |

FOREIGN PATENT DOCUMENTS

| | | |
|---|---|---|
| 0043292 | 8/1982 | European Pat. Off. |
| 2039909 | 8/1980 | United Kingdom |

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane substituted thio prostaglandin analogs are provided having the structural formula

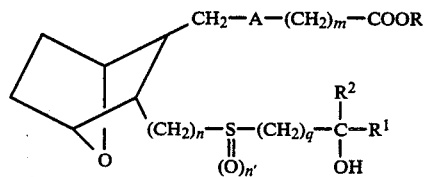

wherein R is hydrogen, lower alkyl, alkali metal, or a polyhydroxylamine salt, $R^1$ is hydrogen, lower alkyl, arylalkyl, aryl, cycloalkyl or cycloalkylalkyl, $R^2$ is hydrogen or lower alkyl, A is —CH=CH— or —(CH$_2$)$_2$, n is 1 to 4, n' is 0, 1 or 2, q is 1 to 10 and m is 0 to 8, and including all stereoisomers thereof.

The compounds are cardiovascular agents useful, for example, in the treatment of thrombotic disease, and as such are useful in inhibiting platelet aggregation.

12 Claims, No Drawings

7-OXABICYCLOHEPTANE SUBSTITUTED THIO PROSTAGLANDIN ANALOGS USEFUL IN THE TREATMENT OF THROMBOLYTIC DISEASE

DESCRIPTION OF THE INVENTION

The present invention relates to 7-oxabicycloheptane thio prostaglandin analogs which are cardiovascular agents useful, for example, in the treatment of thrombotic disease. These compounds have the structural formula

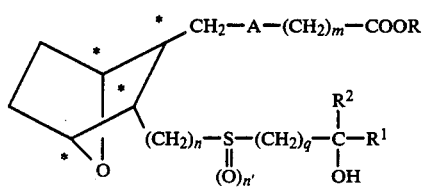

and including all stereoisomers thereof, wherein A is CH=CH or $(CH_2)_2$, m is 0 to 8, n is 1 to 4, n' is 0, 1 or 2, q is 1 to 10, R is H, lower alkyl, alkali metal or a polyhydroxylamine salt, $R^1$ may be hydrogen, lower alkyl, aryl, aralkyl, cycloalkyl or cycloalkylalkyl; and $R^2$ is hydrogen or lower alkyl.

The term "lower alkyl" or "alkyl" as employed herein alone or as part of another group includes both straight and branched chain carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy" or "aralkoxy" as employed herein alone or as part of another group includes any of the above lower alkyl, alkyl or aralkyl groups linked to an oxygen atom.

The terms "$(CH_2)_m$", "$(CH_2)_n$" and "$(CH_2)_q$" include straight or branched chain radicals having from 1 to 8 carbons in the normal chain in the case of "$(CH_2)_m$", from 1 to 4 carbons in the normal chain in the case of "$(CH_2)_n$" and from 1 to 10 carbons in the normal chain in the case of "$(CH_2)_q$" and may contain one or more lower alkyl and/or halogen substituents. Examples of $(CH_2)_m$, $(CH_2)_n$ and $(CH_2)_q$ groups include $CH_2$,

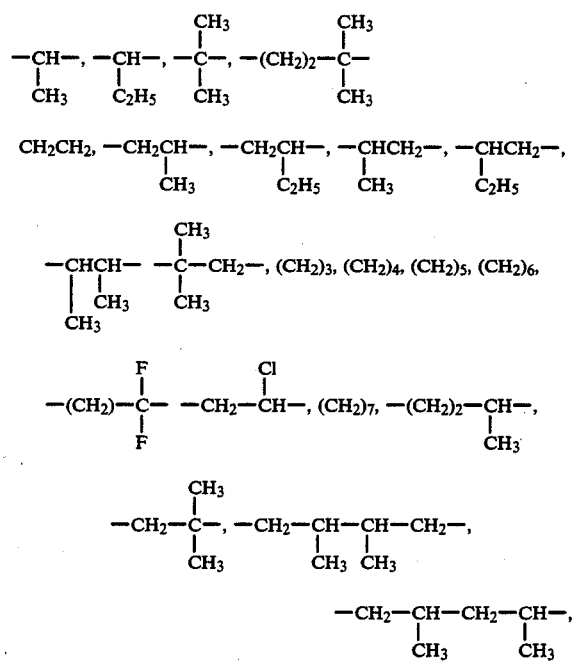

and the like.

Preferred are those compounds of formula I wherein A is CH=CH, m is 2 to 4, R is H, n is 1, n' is 0, q is 1 to 7, $R^1$ is pentyl, hexyl, heptyl, cyclohexyl, cyclohexylmethyl, phenyl, benzyl, 2-phenylethyl or 3-phenylpropyl.

The various compounds of the invention may be prepared as outlined below.

A. Where n = 1

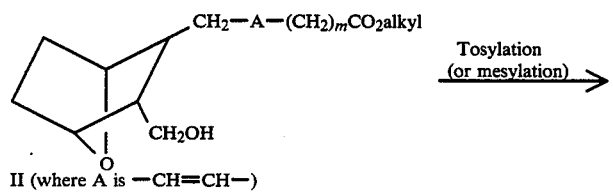

II (where A is —CH=CH—)

Tosylation (or mesylation) →

-continued
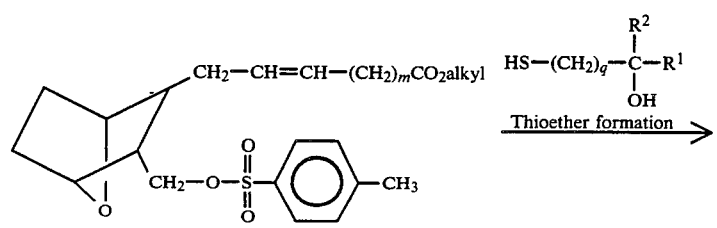
III
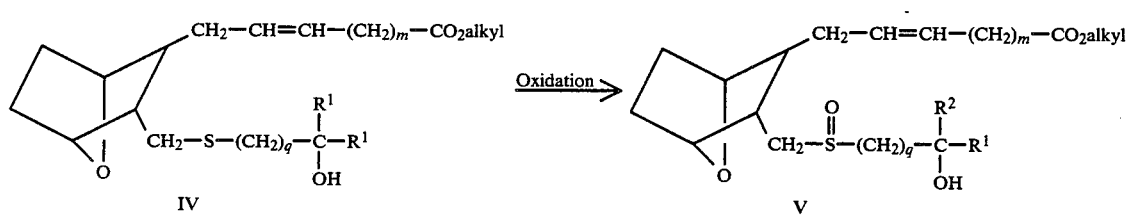
IV      Oxidation →      V
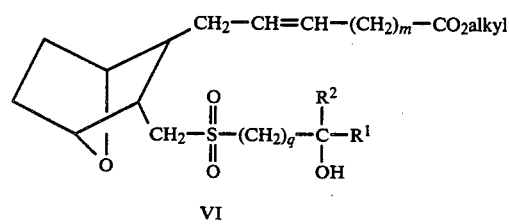
VI
II $\xrightarrow{\text{Reduction}}_{\text{H}_2/\text{Pd/C}}$
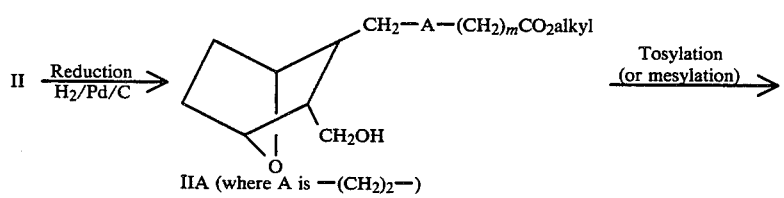
IIA (where A is —(CH$_2$)$_2$—)    Tosylation (or mesylation) →
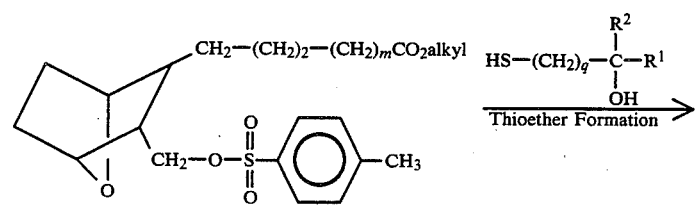
IIIA (where A is —(CH$_2$)$_2$—)
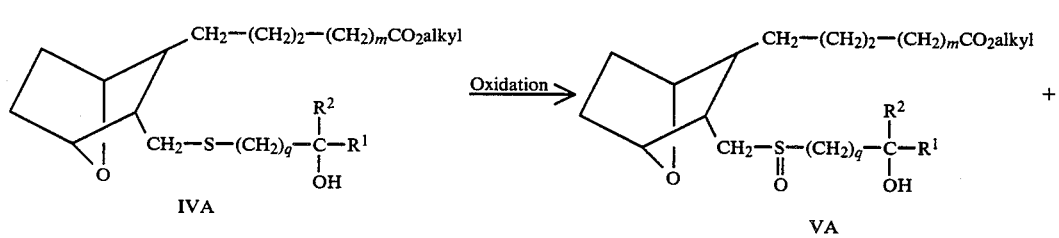
IVA      Oxidation →      VA    +
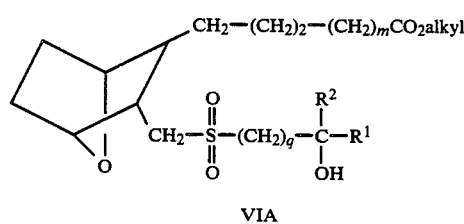
VIA IV, V or VI $\xrightarrow[\text{Alkali metal hydroxide}]{\text{Hydrolysis}}$ (LiOH, NaOH, KOH)

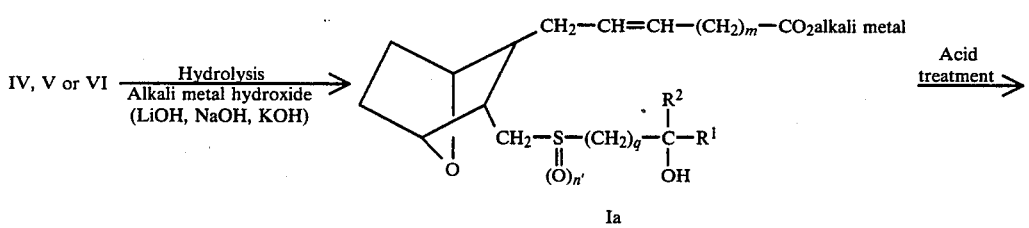

Ia $\xrightarrow{\text{Acid treatment}}$

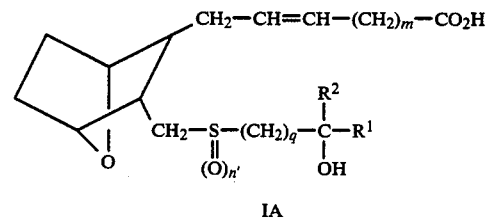

IA

IVA, VA or VIA $\xrightarrow[\text{Alkali metal hydroxide}]{\text{Hydrolysis}}$ (LiOH, NaOH, KOH)

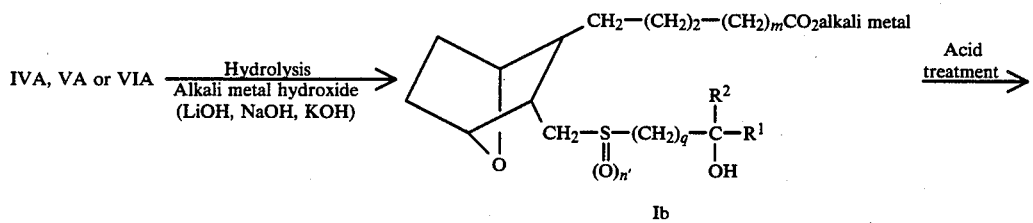

Ib $\xrightarrow{\text{Acid treatment}}$

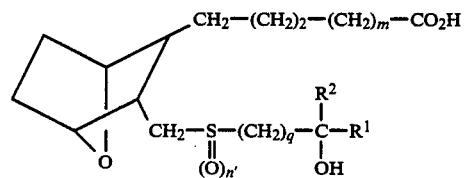

IB

B. Where n is 2 to 4

II or IIA $\xrightarrow{\text{Collins Oxidation}}$

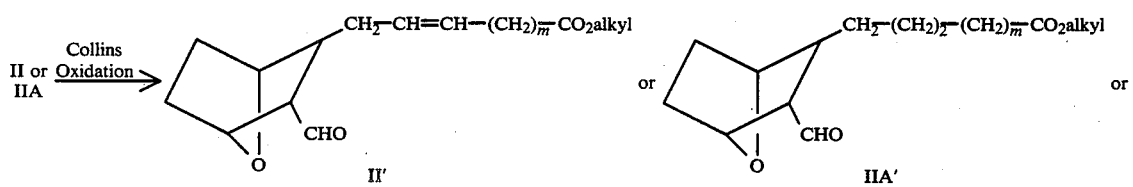

II'    IIA'    or $\xrightarrow[\text{(C}_6\text{H}_5\text{)}_3\text{P}=\text{CHOCH}_3]{\text{Wittig}}$

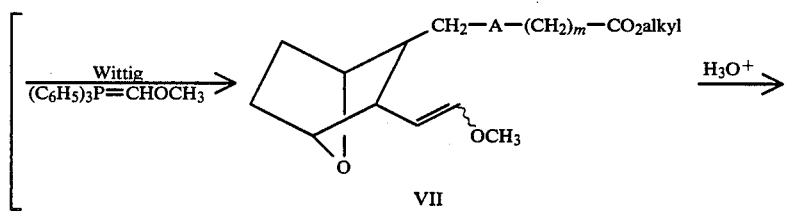

VII $\xrightarrow{\text{H}_3\text{O}^+}$

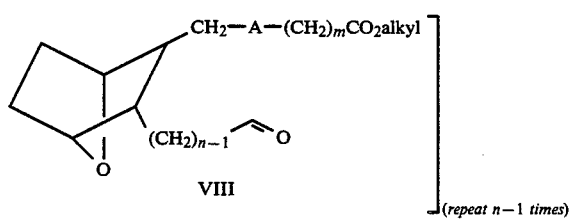

VIII (repeat n−1 times)

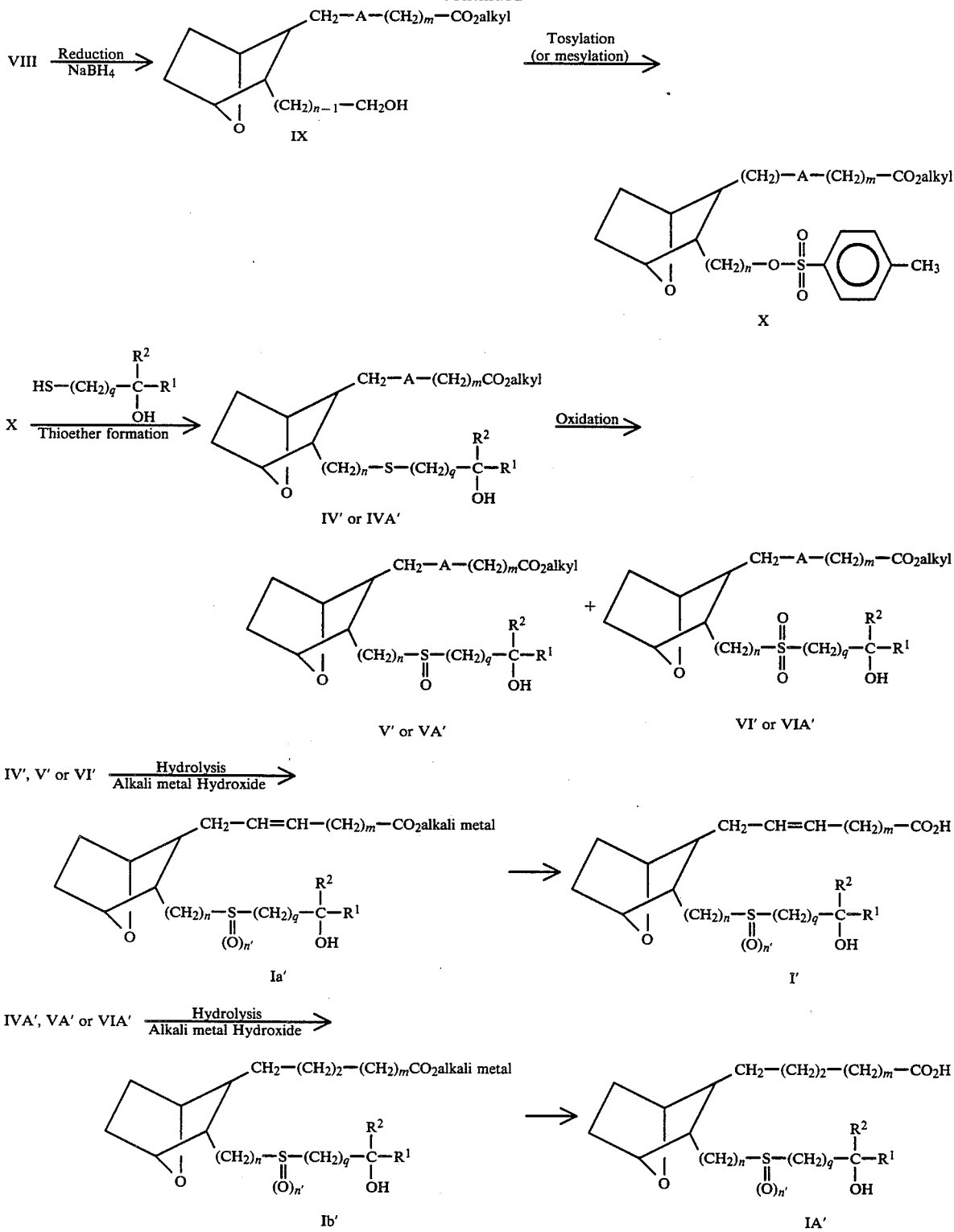

In the reaction sequence identified as "A", where in Formula I n is 1, the lower alkyl ester containing the hydroxymethyl group, that is, compound II (where A is —CH=CH—) or IIA (where A is —(CH$_2$)$_2$) (prepared as described in U.S. Pat. No. 4,143,054) is employed as the starting material. Thus, where A is —CH=CH—, compound II is subjected to a tosylation reaction, for example, by reacting II with tosyl chloride in pyridine to form tosylate III. To form the tosylate IIIA (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a tosylation reaction (or a mesylation reaction) to form tosylate IIIA (or corresponding mesylate) (where A is (CH$_2$)$_2$). Thereafter, tosylate (or mesylate) III or IIIA is reacted with a thiol of the structure

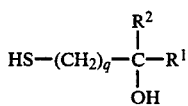
A employing a molar ratio of III or IIIA:thiol of within the range of from about 0.8:1 to about 1:10, in a solvent such as tetrahydrofuran and in the presence of potassium t-butoxide to form the sulfide IV or IVA.

The compounds of formula I may also be prepared as described above except that the tosylate or mesylate III or IIIA is reacted with a thiol derivative A in which the hydroxyl group is protected with any standard protecting group; for example, tetrahydropyranyl thiol B

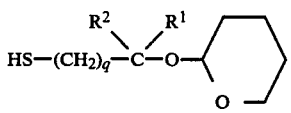
B to form the protected compound C

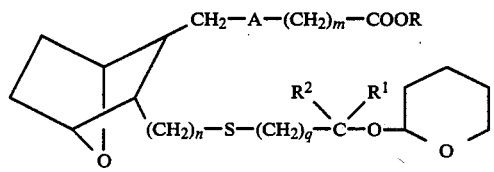
C which is then treated with Amberlyst resin in the presence of methanol to form the ester IV, IVA, IV', and IVA'.

To form the sulfinyl and/or sulfonyl analogs (where n=1), sulfide derivative IV or IVA is subjected to oxidation, for example by reacting same with sodium periodate, in the presence of methanol and tetrahydrofuran, to form the sulfinyl derivative V or VA and the sulfonyl derivative VI or VIA. The above sulfinyl and sulfonyl derivatives may be separated by chromatography or other conventional separation procedures.

In the reaction sequence identified as "B", where in Formula I n is 2 to 4, the starting lower alkyl ester containing the hydroxymethyl group, that is, compound II, (prepared as described in U.S. Pat. No. 4,143,054) is used to form the aldehyde II' (where A is —CH═CH—) or IIA' (where A is —(CH$_2$)$_2$). Thus, to form aldehyde II' where A is —CH═CH—, compound II is subjected to a Collins oxidation, for example, by reacting II with chromium trioxide in pyridine. To form the aldehyde IIA' (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a Collins oxidation to form aldehyde IIA' (where A is (CH$_2$)$_2$).

The aldehyde II' or IIA' is used to prepare aldehyde VIII (where n is 2-4) by carrying out a homologation sequence, such as a Wittig reaction with (C$_6$H$_5$)$_3$P═CHOMe followed by hydrolysis, (n−1) times. The aldehyde VIII (where n is 2-4) is thus carried on to compounds of this invention where n is 2-4, that is

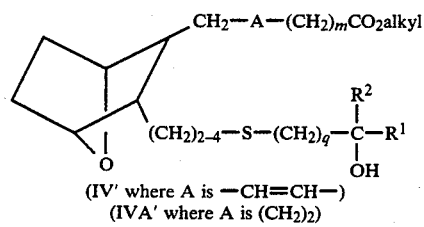
IV' or IVA'

(IV' where A is —CH═CH—)
(IVA' where A is (CH$_2$)$_2$)

by reducing aldehyde VIII employing a reducing agent such as sodium borohydride or sodium cyanoborohydride in a solvent such as methanol to form the alcohol ester IX which is subjected to a tosylation reaction as described above to form tosylate X which in turn is subjected to thioether formation by reaction with

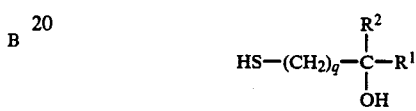
A as described above to form sulfide IV' or IVA'.

The sulfinyl derivative (where n is 2 to 4) and sulfonyl derivatives (where n is 2 to 4) are prepared by subjecting sulfide IV' or IVA' to an oxidation reaction as described above to form a mixture of sulfinyl V' and/or VA', and sulfonyl VI' and/or VIA'.

The above sulfinyl and sulfonyl derivatives may be separated by chromatography or other conventional separation procedures.

The esters IV, V, VI, IVA, VA, VIA, IV', V', VI', IVA', VA', VIA', can be converted to the free acid, that is, to
I (A is CH═CH)
or
I' (A is (CH$_2$)$_2$)

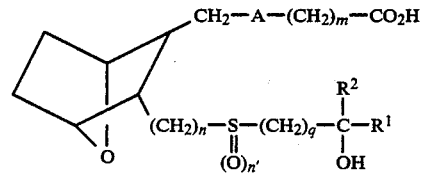

by treating the esters with an alkali metal hydroxide, such as lithium or sodium hydroxide to form the alkali metal salt Ia or Ib or Ia' or Ib', followed by neutralization with an acid, such as dilute hydrochloride acid or oxalic acid to form the acid.

The starting thiol A is generally known. For example, the thiol A may be conveniently prepared from the corresponding alcohols A' using the method of Volante: Tetrahedron Letters 1981, 22, 3119.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

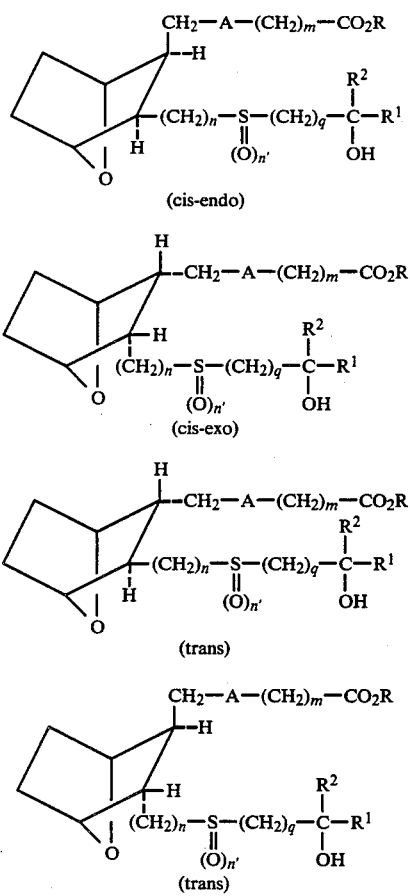

The nucleus in each of the compounds of the invention is depicted as

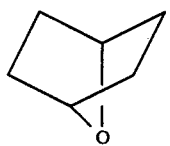

for matter of convenience; it will also be appreciated that the nucleus in the compounds of the invention may be depicted as

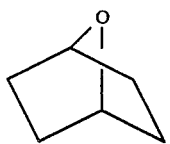

The compounds of this invention are cardiovascular agents useful as platelet aggregation inhibitors of arachidonic acid induced platelet aggregation, e.g., for treatment of thrombolytic disease, such as coronary or cerebral thromboses, and as inhibitors or broncho-constriction associated with asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors and may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade.

EXAMPLE 1

[1S-[1β,2α(Z),3α,4β]]-7-[3-[[(2-Hydroxyethyl)thio]-methyl]-7-oxabicyclo[2.2.1]hept-2-yl]-5-heptenoic acid, methyl ester

A.

[1β,2α(Z),3α,4β]-7-[3-(Hydroxymethyl)-7-oxabicyclo[2.2.1]hept-2-yl]-5-heptenoic acid, methyl ester (a) A mixture of N-acetylpyridinium chloride was prepared by adding 9.6 ml (136 mmole) of acetyl chloride dropwise to 56 ml of pyridine. To this was added 5.0 g (27 mmole) of (exo)-3-(2-methoxyethenyl)-7-oxabicyclo[2.2.1]heptane-2-methanol dissolved in 5 ml of pyridine. The resulting mixture was stirred at room temperature for 1.5 hours and poured into brine. The product was extracted into ether (3×200 ml); the ether extracts were washed with 5% hydrochloric acid (2×400 ml) and brine (1×200 ml) and dried over sodium sulfate. Concentration yielded a yellow oil which was purified by passage through a short column of silica gel (150 ml) with dichloromethane, yield 4.42 g of an oil.

(b) To a solution of 4.42 g (19.6 mmole) of the oil in 500 ml of tetrahydrofuran containing 50 ml of water was added 31.1 g (97.8 mmole) of mercuric acetate. The yellow suspension which formed was stirred for 10 minutes and then the entire mixture was poured into a solution containing 200 g of potassium iodide in 2 l. of water. Upon shaking, the yellow color disappeared and the mixture was extracted with benzene (3×500 ml). The combined benzene extracts were washed with potassium iodide solution and brine and dried over sodium sulfate. Concentration yielded 3.7 g of material which crystallized on standing in an ice box.

(c) A Wittig reagent was prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of the product of part (b) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 500 g of silica gel with 50/50 ethyl acetate-hexane as the eluant which gave 600 mg of acid which crystallized on standing. This was recrystallized twice from ethyl acetate-cyclohexane to yield 320 mg of [1β,2α(Z),3α,4β]-7-[3-(hydroxymethyl)-7-oxabicyclo[2.2.1]hept-2-yl]-5-heptenoic acid.

(d) Following the procedure as set out in Example 7 of U.S. Pat. No. 4,143,054, the acid from part (c) is converted to the corresponding methyl ester.

B.
[1β,2α(Z),3α,4β]-7-[3-(p-Toluenesulfonyloxymethyl)-7-oxabicyclo[2.2.1]hept-2-yl]-5-heptenoic acid, methyl ester To a solution of 300 mg (1.12 mmol) of alcohol ester from Part A in 4 ml of dry pyridine was added 427 mg (2.24 mmol) of tosyl chloride. The mixture was stirred at room temperature under an argon atmosphere for 10 hours. The reaction mixture was diluted with 300 ml of ether, washed with 1N aqueous HCl solution (3×100 ml), and 0.5N aqueous NaOH solution (3×100 ml). The ether layer was dried over anhydrous magnesium sulfate and concentrated in vacuo. Purification was effected by flash chromatography on 30 g of silica gel 60 using 50% hexane in ether as eluant to give 450 mg of title compound (9%). TLC:silica gel, 4% $CH_3OH$ in $CH_2Cl_2$, $R_f$=0.80, iodine.

C.
[1S-[1β,2α(5Z),3α,4β]]-7-[3-[[(2-Hydroxyethyl)thio]methyl]-7-oxabicyclo[2.2.1]-hept-2-yl]-5-heptenoic acid, methyl ester To a stirred solution of 223 mg (1.99 mmol) of potassium t-butoxide in 15 ml of dry THF under argon was added 389 mg (4.98 mmol) of 2-mercaptoethanol. To this mixture was added a solution of 700 mg (1.66 mmol) of Part B tosylate in 20 ml of dry THF. The reaction mixture was refluxed for 8 hours. To this mixture was then added a mixture of 460 mg (4.1 mmol) of potassium t-butoxide and 1.00 ml (14.3 mmol) of 2-mercaptoethanol in 4 ml of dry THF. The reaction mixture was refluxed for another 2 hours. The cooled reaction mixture was diluted with 350 ml of EtOAc and washed with 75 ml of saturated $NaHCO_3$ solution. The EtOAc solution was dried over anhydrous $MgSO_4$, filtered and concentrated in vacuo. This was chromatographed on 60 g of silica gel 60 using hexane-ether 1:2 as eluant to give 440 mg (81%) of title methyl ester as an oil. TLC: silica gel, $R_f$=0.20, hexane-ether 1:2, $Ce(SO_4)_2$.

EXAMPLE 2

[1S-[1β,2α(5Z),3α,4β]]-7-[3-[[(2-Hydroxyethyl)thio]methyl]-7-oxabicyclo[2.2.1]hept-2-yl]-5-heptenoic acid To a stirred solution of 440 mg (1.34 mmol) of Example 1 methyl ester in 60 ml of freshly distilled THF and 12 ml of water was added 13.6 ml of 1N aqueous lithium hydroxide solution. The reaction mixture was purged with argon vigorously for 15 minutes and stirred at room temperature for 5 hours. The reaction mixture was acidified to pH 3 by the addition of 1N aqueous HCl solution and poured into 150 ml of saturated NaCl solution. The resulting solution was saturated with NaCl and extracted with EtOAc (4×200 ml). The combined EtOAc extracts were dried ($MgSO_4$), filtered and concentrated in vacuo. Purification was effected by flash chromatography on 60 g of silica gel 60 using 4% $CH_3OH$ in $CH_2Cl_2$ as eluant to give 370 mg (88%) of desired title acid which was contaminated with a double bond isomer of such acid. This was chromatographed on 120 g of silica gel 60 using 0.25% acetic acid in 4% $CH_3OH/CH_2Cl_2$ as eluant to give 160 mg (38%) of title acid and a mixture of title acid and a double bond isomer (120 mg, 28%). TLC: silica gel, 4% $CH_3OH/CH_2Cl_2$, $R_f$=0.24, iodine.

$[\alpha]_D$= −10.0° (C=0.57, $CHCl_3$).

Anal Calcd for $C_{16}H_{26}O_4S$: C, 61.11; H, 8.33; S, 10.20. Found: C, 60.75; H, 8.47; S, 10.16.

EXAMPLE 3

(1β,2α,3α,4β)-7-[3-[[(2-Hydroxyethyl)thio]methyl]-7-oxabicyclo[2.2.1]hept-2-yl]heptanoic acid, methyl ester A.
(1β,2α,3α,4β)-7-[3-(Hydroxymethyl)-7-oxabicyclo[2.2.1]hept-2-yl]heptanoic acid, methyl ester To 800 mg (3.0 mmole) of the [1β,2α(Z),3α,4β]-7-[3-(hydroxymethyl)-7-oxabicyclo[2.2.1]-hept-2-yl]-5-heptenoic acid, methyl ester as prepared in Example 1, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
(1β,2α,3α,4β)-7-[[3-[(2-Hydroxyethyl)thio]methyl]-7-oxabicyclo[2.2.1]hept-2-yl]heptanoic acid, methyl ester Following the procedure of Example 1 except substituting the Part A alcohol-ester for the Example 1A alcohol ester, the title product is obtained.

EXAMPLE 4

(1β,2α,3α,4β)-7-[3-[[(2-Hydroxyethyl)thio]methyl]-7-oxabicyclo[2.2.1]hept-2-yl]heptanoic acid Following the procedure of Example 2 except substituting the Example 3 methyl ester for the Example 1 methyl ester, the title acid is obtained.

EXAMPLE 5

[1β,2α(Z),3β,4β]-7-[3-[[(2-Hydroxyethyl)thio]-methyl]-7-oxabicyclo[2.2.1]hept-2-yl]-5-heptenoic acid, methyl ester

A.

[1β,2α(Z),3β,4β]-7-[3-(p-Toluenesulfonyloxymethyl)-7-oxabicyclo[2.2.1]hept-2-yl]-5-heptenoic acid, methyl ester To a solution of 510 mg (1.9 mmol) of [1β,2α(Z),3β,4β]-7-[3-(hydroxymethyl)-7-oxabicyclo-[2.2.1]hept-2-yl]-5-heptenoic acid, methyl ester (prepared as described in U.S. Pat. No. 4,143,054) in 10 ml of dry pyridine under argon at 0° C. was added a solution of 730 mg (3.8 mmol) of of tosyl chloride in 10 ml of dry $CH_2Cl_2$. This mixture was allowed to warm to room temperature and stirred for 19 hours. The reaction mixture was poured into 70 ml of a mixture of ice and water and stirred for 40 minutes. The aqueous layer was extracted with ether (3×140 ml). The combined ether extracts were washed with 1N aqueous HCl solution (2×50 ml), saturated $NaHCO_3$ solution (2×50 ml) and brine (1×100 ml). The ether layer was dried ($MgSO_4$), filtered and concentrated in vacuo to give an oily product. This was chromatographed on 66 g of silica gel 60 using 1:1 hexane-ether as eluant to give 650 mg (81%) of desired title tosylate as an oil.

TLC: silica gel, hexane-ether 1:1, $R_f$=0.25, iodine.

Analysis: Calculated for $C_{22}H_{30}O_6S$: C, 62.53; H, 7.16; S, 7.59. Found: C, 62.12, H, 7.23; S, 7.41.

B.

[1β,2α(Z),3β,4β]-7-[3-[[(2-Hydroxyethyl)thio]methyl]-7-oxabicyclo[2.2.1]-hept-2-yl]-5-heptenoic acid, methyl ester Following the procedure of Example 1 except substituting the Part A tosylate for the Example 1B tosylate, the title compound is obtained.

EXAMPLE 6

[1β,2α(Z),3β,4β]-7-[3-[[(2-Hydroxyethyl)thio]-methyl]-7-oxabicyclo[2.2.1]hept-2-yl]-5-heptenoic acid Following the procedure of Example 2 except substituting the Example 5 methyl ester for the Example 1 methyl ester, the title compound is obtained.

EXAMPLE 7

[1S-[1α,2β(Z),3β,4α]]-7-[3-[[(2-Hydroxyhexyl)thio]-methyl]-7-oxabicyclo[2.2.1]hept-2-yl]-5-heptenoic acid, methyl ester [fast moving isomer (FMI) and slow moving isomer (SMI)]

To a stirred solution of 0.98 g (8.71 mmol) of potassium t-butoxide in 10 ml of dry THF under argon atmosphere was added 2-hydroxy-1-hexanethiol (prepared from 1,2-dihydroxyhexane via (1) selective tosylation of the primary hydroxyl group at −20° C., (2) protection of secondary alcohol as the TBDMS ether, (3) displacement of the tosylate with potassium thioacetate in DMSO/THF, and (4) LAH reduction). To this mixture was added a solution of 1.47 g (3.48 mmol) of Example 1, Part B tosylate in 15 ml of dry THF. The reaction mixture was heated to reflux gently for 3 hours and 30 minutes. The cooled reaction mixture was diluted with 800 ml of EtOAc and washed with 200 ml of saturated $NaHCO_3$ solution. The organic layer was dried ($MgSO_4$), filtered and concentrated in vacuo. This was chromatographed on 60 g of silica gel 60 using hexane-ether 2:1 as eluant go give 2.12 g of a mixture of title F.M.I. methyl ester, title S.M.I. methyl ester and the disulfide of 2-hydroxy-1-hexanethiol. The disulfide impurity was removed by chromatography following basic hydrolysis of the above mixture under standard conditions. Esterification of the inseparable pair of carboxylic acids with etheral diazomethane gave a mixture of title F.M.I. methyl ester and title S.M.I. methyl ester. A 200 mg portion of this mixture was separated by semi-prep HPLC using a gradient elution from 1.6% THF in $CH_2Cl_2$ to 3.2% THF in $CH_2Cl_2$; approximately 40 mg was injected each run. This gave 90 mg of title F.M.I. methyl ester, 70 mg of title S.M.I. methyl ester and 40 mg of a mixture of S.M.I. and F.M.I. methyl esters. TLC: silica gel, 4% THF/$CH_2Cl_2$, $R_f$=title F.M.I., 0.42; title SMI, 0.40, iodine.

$[\alpha]_D$ of F.M.I.=12.8° (c=1.46, $CHCl_3$).
$[\alpha]_D$ of S.M.I.=−25.7° (c=4.06, $CHCl_3$).

EXAMPLE 8

[1S-[1α,2β(Z),3β,4α]]-7-[3-[[(2-Hydroxyhexyl)thio]-methyl]-7-oxabicyclo[2.2.1]hept-2-yl]-5-heptenoic acid (fast moving isomer)

To a stirred solution of 82 mg (0.21 mmol) of Example 7 F.M.I. methyl ester in 10 ml of freshly distilled THF was added 1.9 ml of $H_2O$ and 2.2 ml of 1N aqueous lithium hydroxide solution. The reaction mixture was purged with argon vigorously for 15 minutes and stirred at room temperature for 7 hours and 30 minutes. The reaction mixture was acidified to pH 3 by the addition of 1N aqueous HCl solution and poured into 30 ml of brine. The resulting solution was saturated with NaCl and extracted with EtOAc (4×50 ml). The combined EtOAc extracts were dried ($Na_2SO_4$), filtered and concentrated in vacuo. Purification was effected by flash chromatography on 25 g of silica gel 60 using 2% $CH_3OH$ in $CH_2Cl_2$ as eluant to give 70 mg (88%) of title F.M.I. acid as an oil.

TLC: silica gel, 2% $CH_3OH/CH_2Cl_2$, $R_f$=0.22, $I_2$.
$[\alpha]_D$=11.8° (c=3.15, $CHCl_3$).

Anal Calcd for $C_{20}H_{34}O_4S$: C, 64.82; H, 9.25; S, 8.65. $C_{20}H_{34}O_4S$·0.35 mole $H_2O$: C, 63.75; H, 9.28; S, 8.51. Found: C, 63.71; H, 9.16; S, 8.33.

EXAMPLE 9

[1S-[1α,2β(Z),3β,4α]]-7-[3-[[(2-Hydroxyhexyl)thio]-methyl]-7-oxabicyclo[2.2.1]hept-2-yl]-5-heptenoic acid (slow moving isomer)

To a stirred solution of 67.8 mg (0.18 mmol) of Example 7 S.M.I. methyl ester in 8.6 ml of freshly distilled THF was added 1.6 ml of water and 1.9 ml of 1N aqueous lithium solution. The reaction mixture was purged with argon vigorously for 15 minutes and stirred at room temperature for 8 hours and 30 minutes. The reaction mixture was acidified to pH 3 by the addition of 1N aqueous HCl solution and poured into 30 ml of brine. The resulting solution was saturated with NaCl and extracted with EtOAc (4×50 ml). The combined EtOAc extracts were dried ($Na_2SO_4$), filtered and concentrated in vacuo. Purification was effected by flash chromatography on 24 g of silica gel 60 using 2% $CH_3OH/CH_2Cl_2$ as eluant to give 40 mg (61%) of pure title S.M.I. acid as an oil. TLC: silica gel, 2% $CH_3OH/CH_2Cl_2$, $R_f$=0.22, iodine.

Anal Calcd for $C_{20}H_{34}O_4S$: C, 64.82; H, 9.25; S, 8.65. $C_{20}H_{34}O_4S \cdot 0.35$ mole $H_2O$: C, 63.75; H, 9.28; S, 8.51. Found: C, 63.65; H, 9.05; S, 8.46.

EXAMPLE 10

[1β,2α(5Z),3α,4β]-7-[3-[[(8-Hydroxyoctyl)thio]methyl]-7-oxabicyclo[2.2.1]hept-2-yl]-5-heptenoic acid, methyl ester

A.

[1β,2α(Z),3α,4β]-7-[3-(Methylsulfonyloxymethyl)-7-oxabicyclo[2.2.1]hept-2-yl]-5-heptenoic acid, methyl ester To a vigorously stirred solution of 5.00 g (18.7 mmol) of Example 1 Part A alcohol ester and 2.17 ml (28.0 mmol) of mesyl chloride in 40 ml of dichloromethane under argon at $-20°$ C. was added 5.20 ml (37.3 mmol) of triethylamine dropwise. The reaction mixture was stirred at 0° C. for 2 hours. The reaction mixture was diluted with 180 ml of ether. The resulting precipitate was removed by filtration and the filter cake was eluted with additional amount of 80 ml of ether. The combined ether filtrates were concentrated in vacuo and chromatographed on 90 g of Baker's silica gel using 2% $CH_3OH$ in $CH_2Cl_2$ as eluant to give 6.1 g (94%) of title mesylate as a solid. TLC: silica gel, hexane-ether 1:1, $R_f=0.16$, $I_2$.

B.

[1β,2α(Z),3α,4β]-7-[3-[[8-(2-Tetrahydropyranyloxy)octyl]thio]methyl]-7-oxabicyclo[2.2.1]hept-2-yl]-5-heptenoic acid, methyl ester To a stirred solution of 200 mg (1.73 mmol) of potassium t-butoxide in 20 ml of dry THF under argon was added 2-(8-mercapto-octyloxy)-tetrahydropyrane (prepared from 1,8-octanediol via (1) mono-THP ether formation, (2) thioacetate formation with $Ph_3P$, thioacetic acid and diisopropyl azodicarboxylate in THF, (3) $LiAlH_4$ reduction). To this mixture was added a solution of 500 mg (1.45 mmol) of Part A mesylate in 15 ml of dry THF. The reaction mixture was refluxed for 16 hours and 30 minutes. The cooled reaction mixture was diluted with 120 ml of saturated $NH_4Cl$ solution and extracted with ether (4×150 ml). The combined ether extracts were dried ($MgSO_4$), filtered and concentrated in vacuo. The oily residue was treated with ethereal diazomethane and the excess diazomethane was destroyed by the addition of glacial acetic acid. Concentration in vacuo gave a semi-solid mixture. This mixture was triturated with hexane-ether 4:1 to afford 280 mg (56%) of solid title mesylate. The filtrate was concentrated in vacuo. The oily residue was chromatographed on 49.6 g of silica gel 60 using 64 ml of hexane-ether 4:1 as eluant, followed by the elution of 400 ml of hexane-ether 2:1, 480 ml of hexane-ether 1:2 and 350 ml of 10% $CH_3OH$ in $CH_2CL_2$. This gave 180 mg (25%) of title THP-ester as an oil. TLC: silica gel, hexane-ether 1:1, $R_f=0.63$, $I_2$.

C.

[1β,2α(5Z),3α,4β]-7-[3-[[(8-Hydroxyoctyl)thio]methyl]-7-oxabicyclo[2.2.1]hept-2-yl]-5-heptenoic acid, methyl ester To a stirred solution of 170 mg (0.34 mmol) of Part B THP-ester in 5 ml of $CH_3OH$ was added 50 mg of Amberlyst resin. This mixture was stirred for 22 hours at room temperature. The reaction mixture was diluted with 10 ml ether and filtered through a 2" pad of celite. The celite cake was eluted with additional amounts of 40 ml of ether twice. The combined filtrates were concentrated in vacuo. This was chromatographed on 24 g of silica gel 60 using hexane-ether 1:1 as eluant to give 110 mg (78%) of title alcohol methyl ester as an oil. TLC: silica gel, hexane-ether 1:1, $R_f=0.23$, $I_2$.

EXAMPLE 11

[1β,2α(5Z),3α,4β]-7-[3-[[(8-Hydroxyoctyl)thio]methyl]-7-oxabicyclo[2.2.1]hept-2-yl]-5-heptenoic acid To a stirred solution of 100 mg (0.24 mmol) of Example 10 alcohol methyl ester in 6.0 ml of freshly distilled THF and 0.8 ml of water under argon was added 1.0 ml of 1N aqueous lithium hydroxide solution. This mixture was purged with argon vigorously for 10 minutes and stirred at room temperature for 7 hours and 30 minutes. The reaction mixture was acidified to pH 3 by the addition of 1N aqueous HCl solution and poured into 50 ml of saturated NaCl solution. The resulting solution was saturated with NaCl and extracted with EtOAc (4×60 ml). The combined EtOAc extracts were dried ($Na_2SO_4$), filtered and concentrated in vacuo to give 110 mg of an oil compound. Final purification was effected by flash chromatography on 20 g of silica gel 60 using ether as eluant to give 70 mg (72%) of pure title acid as an oil. TLC: silica gel, hexane-ether 1:3, $R_f=0.18$, $I_2$.

Anal Calcd for $C_{22}H_{38}O_4S$: C, 66.29; H, 9.61; S, 8.04. Found: C, 66.07; H, 9.67; S, 7.87.

EXAMPLE 12

[1β,2α(Z),3α,4β]-7-[3-[[(4-Hydroxybutyl)thio]methyl]-7-oxabicyclo[2.2.1]hept-2-yl]-5-heptenoic acid Following the procedure of Examples 1 and 2 except substituting 4-mercaptobutanol for 2-mercaptoethanol, the title compound is obtained.

EXAMPLE 13

[1β,2α(Z),3α,4β]-7-[3-[[(6-Hydroxyhexyl)thio]methyl]-7-oxabicyclo[2.2.1]hept-2-yl]-5-heptenoic acid Following the procedure of Examples 1 and 2 except substituting 6-mercaptohexanol for 2-mercaptoethanol, the title compound is obtained.

EXAMPLE 14

(1β,2α,3α,4β)-7-[3-[[(3-Hydroxyheptyl)thio]-methyl]-7-oxabicyclo[2.2.1]hept-2-yl]heptanoic acid Following the procedure of Examples 3 and 4 except substituting 3-hydroxy-1-heptanethiol for 2-mercaptoethanol, the title compound is obtained.

EXAMPLE 15

[1β,2α(Z),3α,4β]-7-[3-[[(3-Cyclohexyl-2-hydroxy)propyl)thio]methyl]-7-oxabicyclo[2.2.1]hept-2-yl]-5-heptenoic acid Following the procedure of Examples 1 and 2 except substituting 3-cyclohexyl-2-hydroxy-1-propanethiol for 2-mercaptoethanol, the title compound is obtained.

EXAMPLE 16

(1β,2α,3α,4β)-7-[3-[(2-Hydroxy-2-phenylethyl)thio]-methyl]-7-oxabicyclo[2.2.1]hept-2-yl]-heptanoic acid Following the procedure of Examples 3 and 4 except substituting 2-hydroxy-2-phenylethanethiol for 2-mercaptoethanol, the title compound is obtained.

EXAMPLE 17

[1β,2α(Z),3α,4β]-7-[3-[[(3-Hydroxy-3-methyl-4-phenylbutyl)thio]methyl]-7-oxabicyclo[2.2.1]-hept-2-yl]-5-heptenoic acid Following the procedure of Examples 1 and 2 except substituting 3-hydroxy-3-methyl-4-phenylbutyl mercaptan for 2-mercaptoethanol, the title compound is obtained.

EXAMPLE 18

[1β,2α(Z),3β,4β]-7-[3-[[(5-Cyclopentyl-5-hydroxypentyl)thio]methyl]-7-oxabicyclo[2.2.1]hept-2-yl]-5-heptenoic acid Following the procedure of Examples 5 and 6 except substituting 5-cyclopentyl-5-hydroxypentanethiol for 2-mercaptoethanol, the title product is obtained.

EXAMPLE 19

[1β,2α(Z),3β,4β]-7-[3-[[(3-Hydroxypropyl)thio]methyl]-7-oxabicyclo[2.2.1]hept-2-yl]-5-heptenoic acid Following the procedure of Examples 5 and 6 except substituting 3-mercaptopropanol for 2-mercaptoethanol, the title compound is obtained.

EXAMPLE 20

(1β,2α,3α,4β)-7-[3-[[(4-Hydroxynonyl)thio]methyl]-7-oxabicyclo[2.2.1]hept-2-yl]heptanoic acid Following the procedure of Examples 3 and 4 except substituting 4-hydroxy-1-nonanethiol for 2-mercaptoethanol, the title compound is obtained.

EXAMPLE 21

[1β,2α(Z),3α,4β]-7-[3-[[2-(2-Hydroxyethyl)thio]ethyl]-7-oxabicyclo[2.2.1]hept-2-yl]-5-heptenoic acid

A.

[1β,2α(Z),3α,4β]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P+—CH$_2$OCH$_3$Cl$^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl, and extracted with ether (4×200 ml). The combined ether phases were washed with NaCl, saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(Z),3α,4β]-7-[3-(2-oxo)ethyl-7-oxabicyclo[2.2.1]hept-2-yl]-5-heptenoic acid, methyl ester, (B) [1β,2α(Z),3α,4β]-7-[3-(2-methoxy)ethendiyl-7-oxabicyclo[2.2.1]hept-2-yl]-5-heptenoic acid, methyl ester, and (C) [1β,2α(Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1β,2α(Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° C. for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[1β,2α(Z),3α,4β]-7-[3-[[2-(2-Hydroxyethyl)thio]ethyl]-7-oxabicyclo[2.2.1]-hept-2-yl]-5-heptenoic acid Following the procedure of Examples 1 and 2 except substituting the above part B alcohol for the alcohol used in Example 1 Part B, the title compound is obtained.

EXAMPLE 22

[1β,2α(Z),3β,4β]-7-[3-[[2-(2-Hydroxyethyl)thio]-ethyl]-7-oxabicyclo[2.2.1]hept-2-yl]-5-heptenoic acid Following the procedure of Example 21 except substituting [1β,2α(Z),3β,4β]-7-[3-formyl-7-oxabicyclo[2.2.1]hept-2-yl]-5-heptenoic acid, methyl ester for [1β,2α(Z),3α,4β]-7-[3-formyl-7-oxabicyclo[2.2.1]hept-2-yl]-5-heptenoic acid, the title compound is obtained.

EXAMPLE 23

(1β,2α,3α,4β)-7-[3-[[2-(2-Hydroxyethyl)thio]-ethyl]-7-oxabicyclo[2.2.1]hept-2-yl]heptanoic acid Following the procedure of Example 21 except substituting (1β,2α,3α,4β)-7-[3-formyl-7-oxabicyclo[2.2.1]hept-2-yl]heptanoic acid, methyl ester for [1β,2α(Z),3α,4β]-7-[3-formyl-7-oxabicyclo[2.2.1]hept-2-yl]-5-heptenoic acid, methyl ester, the title compound is obtained.

EXAMPLE 24

[1β,2α(Z),3α,4β]-7-[3-[[2-(3-Hydroxybutyl)thio]ethyl]-7-oxabicyclo[2.2.1]hept-2-yl]-5-heptenoic acid Following the procedure of Example 21 except substituting 3-hydroxybutanethiol for 2-mercaptoethanol, the title compound is obtained.

EXAMPLE 25

[1β,2α(Z),3β,4β]-7-[3-[[2-(5-Hydroxy-1-methylpentyl)thio]ethyl]-7-oxabicyclo[2.2.1]hept-2-yl]-5-heptenoic acid Following the procedure of Example 22 except substituting 5-mercaptohexanol for 2-mercaptoethanol, the title compound is obtained.

EXAMPLE 26

(1β,2α,3α,4β)-7-[3-[[2-(5-Hydroxyheptyl)thio]-ethyl]-7-oxabicyclo[2.2.1]hept-2-yl]heptanoic acid Following the procedure of Example 23 except substituting 5-hydroxy-1-heptanethiol for 2-mercaptoethanol, the title compound is obtained.

EXAMPLE 27

[1β,2α(Z),3α,4β]-7-[3-[[2-(4-Cyclopentyl-3-hydroxyhexyl)thio]ethyl]-7-oxabicyclo[2.2.1]hept-2-yl]-5-heptenoic acid Following the procedure of Example 21 except substituting 4-cyclopentyl-3-hydroxy-1-hexanethiol for 2-mercaptoethanol, the title compound is obtained.

EXAMPLE 28

[1β,2α(Z),3β,4β]-7-[3-[[2-(2-Hydroxy-2-phenylethyl)thio]ethyl]-7-oxabicyclo[2.2.1]hept-2-yl]-5-heptenoic acid Following the procedure of Example 22 except substituting 2-hydroxy-2-phenylethanethiol for 2-mercaptoethanol, the title compound is obtained.

EXAMPLE 29

[1β,2α(Z),3α,4β]-7-[3-[[2-(2-Hydroxy-3-ethyl-4-phenylpentyl)thio]ethyl]-7-oxabicyclo[2.2.1]-hept-2-yl]-5-heptenoic acid Following the procedure of Example 21 except substituting 2-hydroxy-3-ethyl-4-phenylpentyl mercaptan for 2-mercaptoethanol, the title compound is obtained.

EXAMPLE 30

[1β,2α(Z),3α,4β]-7-[3-[[4-(2-Hydroxyethyl)thio]-butyl]-7-oxabicyclo[2.2.1]hept-2-yl]-5-heptenoic acid

A.

[1β,2α(Z),3α,4β]-7-[3-(3-Oxo)propyl-7-oxabicyclo[2.2.1]hept-2-yl]-5-heptenoic acid, methyl ester Following the procedure of Example 21 Part A except substituting [1β,2α(Z),3α,4β]-7-[3-(2-oxo)-ethyl-7-oxabicyclo[2.2.1]hept-2-yl]-5-heptenoic acid, methyl ester for [1β,2α(Z),3α,4β]-7-[3-formyl-7-oxabicyclo[2.2.1]hept-2-yl]-5-heptenoic acid, methyl ester, the title A compound is obtained.

B.

[1β,2α(Z),3α,4β]-7-[3-(4-Oxo)butyl-7-oxabicyclo[2.2.1]hept-2-yl]-5-heptenoic acid, methyl ester Following the procedure of Example 21 Part A except substituting the aldehyde from Part A above for [1β,2α(Z),3α,4β]-7-[3-formyl-7-oxabicyclo-[2.2.1]hept-2-yl]-5-heptenoic acid, methyl ester, the title B compound is obtained.

C.

[1β,2α(Z),3α,4β]-7-[3-(4-Hydroxybutyl)-7-oxabicyclo[2.2.1]hept-2-yl]-5-heptenoic acid, methyl ester Following the procedure of Example 21 Part B except substituting the title B aldehyde for [1β,2α(Z),3α,4β]-7-[3-(2-oxo)ethyl]-7-oxabicyclo-[2.2.1]hept-2-yl]-5-heptenoic acid, methyl ester, the title C alcohol is obtained.

D.

[1β,2α(Z),3α,4β]-7-[3-[[4-(2-Hydroxyethyl)thio]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 31

[1β,2α(Z),3α,4β]-7-[3-[[4-(2-Hydroxypropyl)thio]-butyl]-7-oxabicyclo[2.2.1]hept-2-yl]-5-heptenoic acid Following the procedure of Example 30 except substituting 2-hydroxypropanethiol for 2-mercaptoethanol, the title compound is obtained.

EXAMPLE 32

[1β,2α(Z),3α,4β]-7-[3-[[4-(5-Hydroxyoctyl)thio]butyl]-7-oxabicyclo[2.2.1]hept-2-yl]-5-heptenoic acid Following the procedure of Example 31 except substituting 5-hydroxyoctanethiol for 2-mercaptoethanol, the title compound is obtained.

EXAMPLE 33

[1β,2α(Z),3α,4β]-7-[3-[[4-(2-Hydroxy-2-phenylethyl)-thio]butyl]-7-oxabicyclo[2.2.1]hept-2-yl]-5-heptenoic acid Following the procedure of Example 31 except substituting 2-hydroxy-2-phenylethanethiol for 2-mercaptoethanol, the title compound is obtained.

EXAMPLE 34

[1β,2α(Z),3α,4β]-7-[3-[[4-(3-Cyclohexyl-2-hydroxypropyl)thio]butyl]-7-oxabicyclo[2.2.1]hept-2-yl]-5-heptenoic acid Following the procedure of Example 31 except substituting 3-cyclohexyl-2-hydroxy-1-propanethiol for 2-mercaptoethanol, the title compound is obtained.

EXAMPLE 35

[1β,2α(Z),3α,4β]-7-[3-[[(2-Hydroxyethyl)sulfinyl]methyl]-7-oxabicyclo[2.2.1]hept-2-yl]-5-heptenoic acid, methyl ester To a solution of 540 mg (1.72 mmol) of [1β,2α(Z),3α,4β]-7-[3-(2-hydroxyethyl)thio]methyl-7-oxabicyclo[2.2.1]hept-2-yl]-5-heptenoic acid, methyl ester (prepared as described in Example 1) in 6.78 ml of methanol at 0° C. is added dropwise over 4 minutes 8.37 ml of 0.5M aqueous sodium periodate solution. Tetrahydrofuran (2 ml) is then added and the resulting reaction mixture is stirred at room temperature for 15 hours. A white precipitate is removed by filtration and washed with ether (3×50 ml). The filtrate is washed with 60 ml of saturated aqueous NaHCO$_3$ solution and dried over anhydrous magnesium sulfate. Concentration in vacuo affords an oily crude product. This is chromatographed on silica gel 60 using 0.5-1.0% CH$_3$OH in CH$_2$Cl$_2$ as eluant to give the title compound.

EXAMPLE 36

[1β,2α(Z),3α,4β]-7-[3-[[(2-Hydroxyethyl)sulfonyl]methyl]-7-oxabicyclo[2.2.1]hept-2-yl]-5-heptenoic acid To a stirred solution of 135 mg (0.41 mmol) of [1β,2α(Z),3α,4β]-7-[3-[[(2-hydroxyethyl)sulfonyl]methyl]-7-oxabicyclo[2.2.1]hept-2-yl]-5-heptenoic acid, methyl ester (Example 35) in 20.3 ml of THF and 3.09 ml of H₂O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried (MgSO₄), filtered and concentrated in vacuo to give the crude acid. Purification is effected by flash chromatography on silica gel 60 using 3% CH₃OH in CH₂Cl₂ as eluant. This affords the title acid.

EXAMPLES 37 TO 51

Following the procedures outlined in the specification and described in the above working Examples, the following compounds may be prepared.

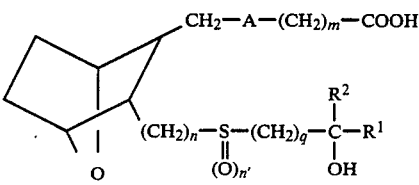

| Ex. No. | A | m | n | n' | q | R¹ | R² |
|---|---|---|---|---|---|---|---|
| 37. | (CH₂)₂ | 0 | 1 | 2 | 1 | ⌬-CH₂ | H |
| 38. | (CH₂)₂ | 2 | 2 | 2 | 2 | ⬠-(CH₂)₂ | CH₃ |
| 39. | CH=CH | 4 | 3 | 2 | 3 | ⌬-(CH₂)₂ | H |
| 40. | (CH₂)₂ | 6 | 4 | 1 | 4 | C₉H₁₉ | C₄H₉ |
| 41. | CH=CH | 8 | 4 | 1 | 8 | C₇H₁₅ | H |
| 42. | (CH₂)₂ | 0 | 3 | 2 | 2 | C₂H₅ | C₃H₇ |
| 43. | (CH₂)₂ | 1 | 2 | 2 | 3 | CH₃ | H |
| 44. | CH=CH | 3 | 1 | 0 | 9 | ⬡-CH₂ | H |
| 45. | (CH₂)₂ | 5 | 1 | 0 | 3 | ⬢-(CH₂)₂ | CH₃ |
| 46. | (CH₂)₂ | 7 | 2 | 2 | 2 | C₆H₅ | CH₃ |
| 47. | (CH₂)₂ | 0 | 3 | 2 | 1 | ⬡ | C₂H₅ |
| 48. | CH=CH | 0 | 4 | 1 | 2 | ⬠ | C₂H₅ |

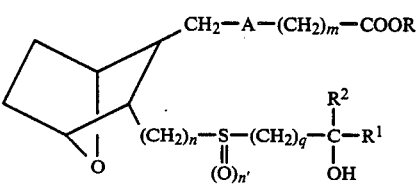

| Ex. No. | A | m | n | n' | q | R¹ | R² |
|---|---|---|---|---|---|---|---|
| 49. | CH=CH | 2 | 3 | 2 | 8 | ⌬-(CH₂)₂ | H |
| 50. | (CH₂)₂ | 3 | 2 | 2 | 3 | ▢ | CH₃ |
| 51. | (CH₂)₂ | 4 | 1 | 2 | 2 | CH₃ | CH₃ |

What is claimed is:

1. A compound having the structural formula

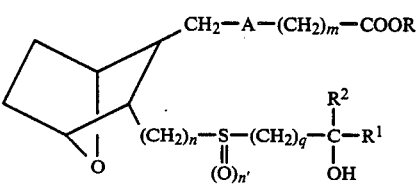

(with COOR)

and including all stereoisomers thereof, wherein A is —CH=CH— or —(CH₂)₂—;

m is 0 to 8; n is 1 to 4; n' is 0, 1 or 2; q is 1 to 10;

R is hydrogen, lower alkyl, alkali metal or a polyhydroxylamine salt; and R¹ is hydrogen, lower alkyl, aryl, aralkyl, cycloalkyl or cycloalkylalkyl, and R² is hydrogen or lower alkyl, wherein lower alkyl or alkyl alone or as part of another group contains 1 to 12 carbons and is unsubstituted or is substituted with halo, hydroxy, alkylamino, alkylthio, CF₃, alkoxy, aryl, alkyl-aryl, haloaryl, cycloalkyl or alkylcycloalkyl;

aryl alone or as part of another group contains 6 to 10 carbons in the ring portion and is unsubstituted or is substituted with 1 or 2 lower alkyl groups, 1 or 2 halogens, 1 or 2 hydroxy groups, 1 or 2 lower alkoxy groups, 1 or 2 alkylamino groups, and/or 1 or 2 alkylthio groups;

cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxyl groups, 1 or 2 alkylamino groups, and/or 1 or 2 alkylthio groups; and (CH₂)ₘ, (CH₂)ₙ and (CH₂)_q include straight or branched chain radicals which may contain 1 or 2 lower alkyl and/or halo substituents.

2. The compound as defined in claim 1 wherein A is —CH=CH—.

3. The compound as defined in claim 1 wherein R is H and R² is H.

4. The compound as defined in claim 1 wherein n' is 0.

5. The compound as defined in claim 1 wherein A is —CH=CH—, m is 2 to 4, n is 1 or 2, n' is 0, q is 1 or 2; R¹ is lower alkyl or cycloalkyl; and R² is hydrogen.

6. The compound as defined in claim 1 wherein A is —CH=CH—, m is 3, n is 1, n' is 0, q 1 or 2, R is H or CH$_3$, R$^1$ is lower alkyl and R$^2$ is H.

7. The compound as defined in claim 1 having the name [1β,2α(5Z),3α,4β]-7-[3-[[(8-hydroxyoctyl)thio]methyl]-7-oxabicyclo[2.2.1]hept-2-yl]-5-heptenoic acid or the methyl ester thereof, including all stereoisomers thereof.

8. The compound as defined in claim 1 having the name [1S-[1α,2β(Z),3β,4α]]-7-[3-[[(2-hydroxyhexyl)thio]methyl]-7-oxabicyclo[2.2.1]hept-2-yl]-5-heptenoic acid or its methyl ester, including all stereoisomers thereof.

9. The compound as defined in claim 1 having the name [1S-[1β,2α(5Z),3α,4β]]-7-[3-[[(2-hydroxyethyl)thio]methyl]-7-oxabicyclo[2.2.1]hept-2-yl]-5-heptenoic acid or its methyl ester, including all stereoisomers thereof.

10. A method of inhibiting platelet aggregation or inhibiting bronchoconstriction, which comprises administering to a mammalian host an effective amount of a compound as defined in claim 1 or a pharmaceutically acceptable salt thereof.

11. The method as defined in claim 10 wherein said compound is administered in an amount within the range of from about 1 to about 100 mg/kg.

12. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

* * * * *